(12) United States Patent
Green

(10) Patent No.: US 6,558,420 B2
(45) Date of Patent: May 6, 2003

(54) DURABLE FLEXIBLE ATTACHMENT COMPONENTS FOR ACCOMMODATING INTRAOCULAR LENS

(75) Inventor: George F. Green, St. Louis, MO (US)

(73) Assignee: Bausch & Lomb Incorporated, Rochester, NY (US)

( * ) Notice: Subject to any disclaimer, the term of this patent is extended or adjusted under 35 U.S.C. 154(b) by 103 days.

(21) Appl. No.: 09/735,115

(22) Filed: Dec. 12, 2000

(65) Prior Publication Data

US 2002/0072795 A1 Jun. 13, 2002

(51) Int. Cl.[7] .................................................. A61F 2/16
(52) U.S. Cl. ................................................... 623/6.34
(58) Field of Search ........................ 623/6.2, 6.34–6.36, 623/6.37, 6.38, 6.43, 6.44, 6.5, 6.51, 6.56, 6.27, 6.32

(56) References Cited

U.S. PATENT DOCUMENTS

| | | | |
|---|---|---|---|
| 4,386,039 A | 5/1983 | Szycher | 264/1.1 |
| 4,846,833 A | 7/1989 | Cumming | 623/6 |
| 4,994,082 A | 2/1991 | Richards et al. | 623/6 |
| 5,047,051 A | 9/1991 | Cumming | 623/6 |
| 5,275,623 A | 1/1994 | Sarfarazi | 623/6 |
| 5,326,347 A | 7/1994 | Cumming | 623/6 |
| 5,476,514 A | 12/1995 | Cumming | 623/6 |
| 5,489,302 A | 2/1996 | Skottum | 623/6 |
| 5,496,366 A | 3/1996 | Cumming | 623/6 |
| 5,674,282 A | 10/1997 | Cumming | 623/6 |
| 5,928,282 A * | 7/1999 | Nigam | 623/6.43 |

(List continued on next page.)

FOREIGN PATENT DOCUMENTS

| | | |
|---|---|---|
| DE | 195 01 444 A1 | 1/1995 |
| EP | 0 435 525 A2 | 7/1991 |
| EP | 0 435 525 A3 | 7/1991 |
| WO | WO 00/66037 | 11/2000 |
| WO | WO 01/34067 A1 | 5/2001 |

OTHER PUBLICATIONS

Article: Accomodative Intraocular Lens with Spring Action Part 1—Design and Placement in an Excised Animal Eye Authors: Tsutomu Hara, M.D., Takako Hara, M.D., Akhiro Yasuda, and Yoshiharu Yamada p. 6 Date: Feb. 1990.

Article: Accomodative Intraocular Lens with Spring Action Part 2.—Fixation in the Living Rabbit Authors: Tsutomu Hara, M.D., Takako Hara, M.D., Akihiro Yasuda, Eng., Yuriko Mizumoto, Eng. and Yasuharu Yamada Eng. p. 4 Date: Sep. 1992.

*Primary Examiner*—David H. Willse
*Assistant Examiner*—Suzette J. Jackson
(74) *Attorney, Agent, or Firm*—Rita D. Vacca (57) ABSTRACT

An accommodating intraocular lens including a higher diopter positive intraocular lens and a lower diopter negative intraocular lens. The positive intraocular lens includes a positive optic portion having an outer peripheral edge and two or more polyurethane elastomer flexible attachment components. The negative intraocular lens includes a negative optic portion having an outer peripheral edge and two or more polyurethane elastomer flexible attachment components. Each flexible attachement component is durable and formed to have specific flexibility characteristics so as to be less resistant to bending in a plane generally parallel to an eye's optical axis than in a plane generally perpendicular to the eye's optical axis. The subject durable accommodating intraocular lens enables axial displacement of the positive optic portion with respect to the negative optic portion along the eye's optical axis under a compression force. The flexible attachment components are durable to allow dependable flexation thereof millions of times during a patient's lifetime. Through this flexation of the flexible attachment components and axial displacement of the positive optic portion with respect to the negative optic portion, accommodative effects are maximized to achieve multi-distance visual imaging.

23 Claims, 6 Drawing Sheets

U.S. PATENT DOCUMENTS

| | | | | |
|---|---|---|---|---|
| 5,964,744 | A | * 10/1999 | Balbierz et al. | 604/530 |
| 5,968,094 | A | * 10/1999 | Werblin et al. | 623/6.32 |
| 6,113,633 | A | * 9/2000 | Portney | 623/6.32 |
| 6,129,759 | A | * 10/2000 | Chambers | 623/6.17 |
| 6,197,058 | B1 | * 3/2001 | Portney | 623/6.34 |
| 6,228,115 | B1 | * 5/2001 | Hoffmann et al. | 623/6.49 |
| 6,231,603 | B1 | * 5/2001 | Lang et al. | 623/6.37 |
| 6,277,149 | B1 | * 8/2001 | Christ et al. | 623/6.56 |
| 6,398,809 | B1 | * 6/2002 | Hoffmann et al. | 623/6.49 |
| 6,461,384 | B1 | * 10/2002 | Hoffmann et al. | 623/6.51 |

* cited by examiner figure 1 figure 2 figure 3 figure 4 figure 5 figure 6 figure 7 figure 8 figure 9 figure 10 figure 11

DURABLE FLEXIBLE ATTACHMENT COMPONENTS FOR ACCOMMODATING INTRAOCULAR LENS

FIELD OF THE INVENTION

The present invention relates to a durable accommodating intraocular lens (IOL) and a method for making and using the same. More particularly, the present invention relates to durable flexible attachment components for an accommodating IOL designed for multi-distance visual imaging in aphakic eyes where a natural lens has been surgically removed, such as in the case of cataracts.

BACKGROUND OF THE INVENTION

Intraocular lens (IOL) implants have been used for many years in aphakic eyes as replacements for natural crystalline lenses that have been surgically removed from the eyes. Many different IOL designs have been developed over past years and proven successful for use in aphakic eyes. Successful IOL designs to date primarily include an optic portion with supports therefor, called haptics, connected to and surrounding at least part of the optic portion. The haptic portions of an IOL are designed to support the optic portion of the IOL in the lens capsule, anterior chamber or posterior chamber of an eye.

Commercially successful IOLs have been made from a variety of biocompatible materials, ranging from more rigid materials such as polymethylmethacrylate (PMMA) to softer, more flexible materials capable of being folded or compressed such as silicones, certain acrylics, and hydrogels. Haptic portions of the IOLs have been formed separately from the optic portion and later connected thereto through processes such as heat, physical staking and/or chemical bonding. Haptics have also been formed as an integral part of the optic portion in what is commonly referred to as "single-piece" IOLs.

Softer, more flexible IOLs have gained in popularity in more recent years due to their ability to be compressed, folded, rolled or otherwise deformed. Such softer IOLs may be deformed prior to insertion thereof through an incision in the cornea of an eye. Following insertion of the IOL in an eye, the IOL returns to its original pre-deformed shape due to the memory characteristics of the soft material. Softer, more flexible IOLs as just described may be implanted into an eye through an incision that is much smaller, i.e., 2.8 to 3.2 mm, than that necessary for more rigid IOLs, i.e., 4.8 to 6.0 mm. A larger incision is necessary for more rigid IOLs because the lens must be inserted through an incision in the cornea slightly larger than the diameter of the inflexible IOL optic portion. Accordingly, more rigid IOLs have become less popular in the market since larger incisions have been found to be associated with an increased incidence of postoperative complications, such as induced astigmatism.

After IOL implantation, both softer and more rigid IOLs are subject to compressive forces exerted on the outer edges thereof from natural brain-induced contraction and relaxation of the ciliary muscles and increases and decreases in vitreous pressure. Compressive forces of this kind are useful in a phakic eye for focusing the eye at various distances. Most commercially successful IOL designs for use in aphakic eyes have single focus optic portions that are fixed and focus the eye at only a certain fixed distance. Such fixed single focus IOLs require the wearing of glasses to change the focus of the eye. A few fixed bifocal IOLs have been introduced to the commercial market but suffer from the disadvantage that each bifocal image represents only about forty percent of the available light thus lessening visual acuity. Accommodating IOLs designed to have two optics held together by flexible loops or straps have also been proposed. However, the flexible attachment components of accommodating IOLs must flex millions of times during a patient's lifetime. Very few materials can withstand such stresses in an aqueous environment without cracking and failing.

Because of the noted shortcomings of current IOL materials, there is a need for an IOL material capable of providing the rigidity required for supporting an IOL optic, capable of being manufactured into small dimensions to fit into the required anatomical space of an eye and capable of withstanding the stresses of accommodation overtime in an aqueous environment without cracking and failing.

SUMMARY OF THE INVENTION

The present invention is the use of polyurethane elastomers to manufacture flexible attachment components for accommodating intraocular lenses (IOL). Although the polyurethane elastomer flexible attachment components of the subject invention may be used for durable function and support in any suitable accommodating IOL design, for purposes of explanation not limitation, particular accommodating IOL designs are described herein. In one accommodating IOL design, the polyurethane elastomer flexible attachment components of the present invention are used to permanently or removably attach preferably a positive IOL optic to a negative IOL optic. The positive IOL optic has a "higher" diopter, preferably approximately +20 diopter or greater, such as but not limited to +20 to +60 diopter, with an outer peripheral edge and two or more but preferably two, three or four polyurethane elastomer flexible attachment components for durable support and function within a patient's eye. The negative IOL optic has a "lower" diopter, preferably approximately −10 diopter or less, such as but not limited to −10 to −50 diopter, also with an outer peripheral edge and preferably the same, but optionally a different number of polyurethane elastomer flexible attachment components from that of the positive optic portion. Positive and negative IOL optics each having two polyurethane elastomer flexible attachment components are balanced for stability within an eye to minimize decentration by having the flexible attachment component integrally formed with or subsequently attached to two opposed edges of each of the two optic portions. Positive and negative IOL optics each having three polyurethane elastomer flexible attachment components are balanced to achieve stability and minimize decentration by having a set of two flexible attachment components integrally formed with or subsequently attached to one edge of each of the optic portions and a third flexible attachment component integrally formed with or subsequently attached to an opposite edge of each of the optic portions. Positive and negative IOL optics each having four polyurethane elastomer flexible attachment components are balanced to achieve stability and minimize decentration by each optic portion having a set of two flexible attachment components integrally formed with or subsequently attached to one edge of the optic and a set of two flexible attachment components integrally formed with or subsequently attached to an opposite edge of the optic. Each polyurethane elastomer flexible attachment component has an attachment portion that permanently connects the flexible attachment component to the outer peripheral edge of an optic portion. If the flexible attachment component is of a looped design, the flexible attachment component has generally two attachment portions that permanently connect the looped flexible attachment component to the outer peripheral edge of the optic portion. In the case of lenses having three or four looped flexible attachment components, a set of two looped flexible attachment components may have three attachment portions rather than four. In such a case, one of the three attachment portions is common to each of the two looped flexible attachment components in the set. Each polyurethane elastomer flexible attachment component whether of a loop design or not includes a flexible central portion located between the attachment portion and a contact plate. The contact plate is designed to engage an inner surface of a patient's eye. The flexible central portions that extend between the contact plates and the attachment portions allow the optic portions of both the positive and negative IOLs to move or to adjust to pressures exerted on the positive and negative lenses within the eye. Additionally, within these flexible central portions, each polyurethane elastomer flexible attachment component is designed to have less resistance to bending in a plane generally parallel to the optical axis of an eye than in a plane generally perpendicular to the optical axis of an eye. By providing polyurethane elastomer flexible attachment components with significantly superior flexibility and durability characteristics, accommodating IOLs are capable of providing accommodative visual effects throughout a patient's lifetime.

Accordingly, it is an object of the present invention to provide flexible and durable accommodating IOLs for use in aphakic eyes.

Another object of the present invention is to provide accommodating IOLs for use in aphakic eyes having flexible and durable attachment components.

Another object of the present invention is to provide a durable material for use in the manufacture of accommodating IOLs.

Another object of the present invention is to provide accommodating IOLs for use in aphakic eyes, which are relatively easy to manufacture.

Still another object of the present invention is to provide accommodating IOLs, which are durable and resistant to decentration within the eyes.

These and other objectives and advantages of the present invention, some of which are specifically described and others that are not, will become apparent from the detailed description, drawings and claims that follow, wherein like features are designated by like numerals.

DETAILED DESCRIPTION OF THE INVENTION

Figure 1:
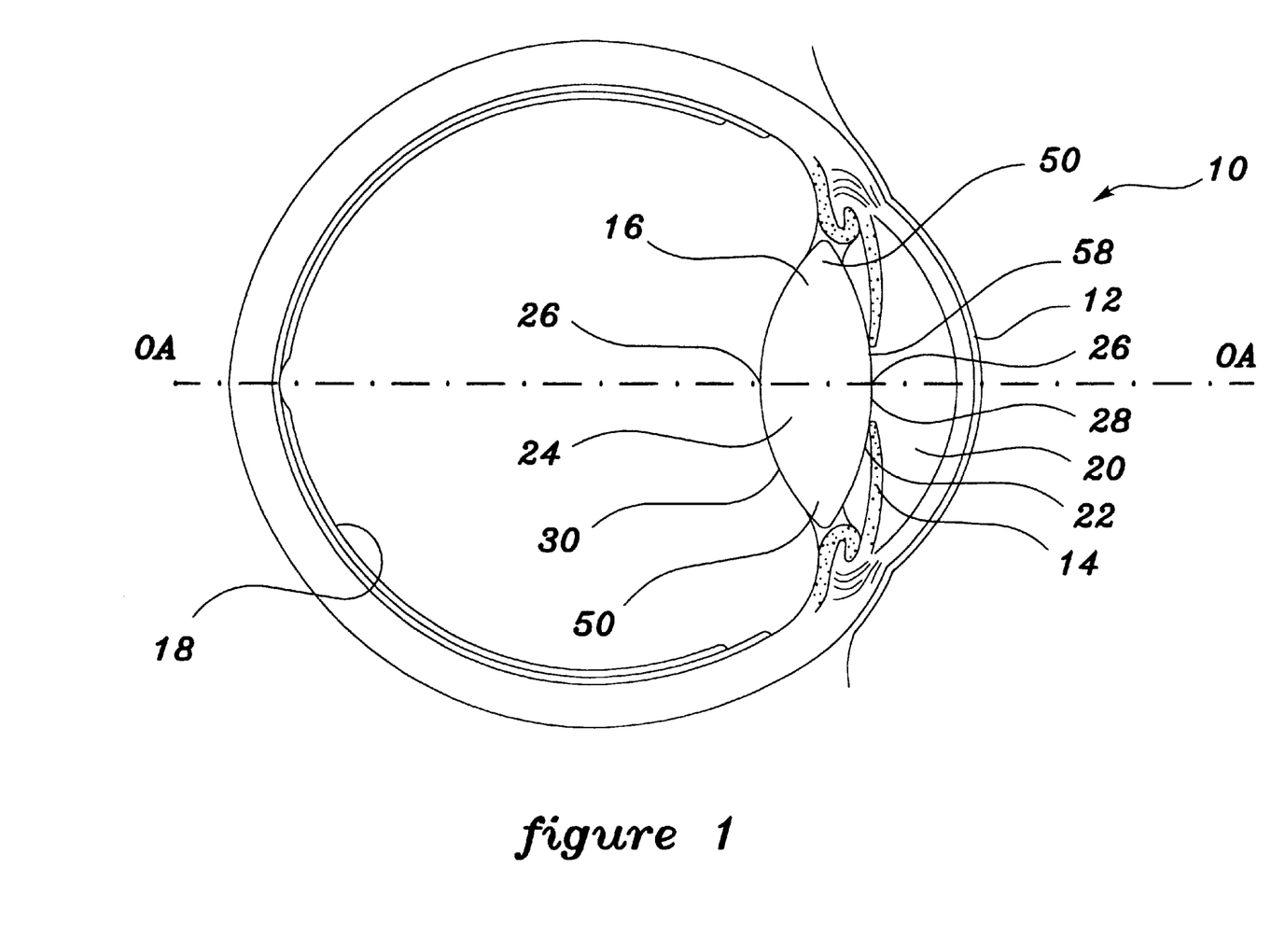
FIG. 1 is a schematic representation of the interior of a human eye.

FIG. 1 illustrates a simplified diagram of an eye 10 showing landmark structures relevant to the implantation of an intraocular lens (IOL) with polyurethane elastomer flexible attachment components of the present invention. Eye 10 includes an optically clear cornea 12 and an iris 14. A natural crystalline lens 16 and a retina 18 are located behind the iris 14 of eye 10. Eye 10 also includes anterior chamber 20 located in front of iris 14 and a posterior chamber 22 located between iris 14 and natural lens 16. An accommodating IOL 32 would most typically be implanted in lens capsule 24 of posterior chamber 22. Flexible attachment components 40 for accommodating IOL 32 of the present invention are manufactured from polyurethane elastomers to achieve the durability required of accommodating IOLs. Flexible attachment components 40 of accommodating IOL 32 must be durable to flex millions of times during a patient's lifetime. An accommodating IOL 32 is typically implanted in lens capsule 24 after the removal of natural lens 16. Eye 10 also includes an optical axis OA—OA that is an imaginary line that passes through the optical center 26 of anterior surface 28 and posterior surface 30 of natural lens 16. Optical axis OA—OA in the human eye 10 is generally perpendicular to a portion of cornea 12, natural lens 16 and retina 18.

Figure 2:
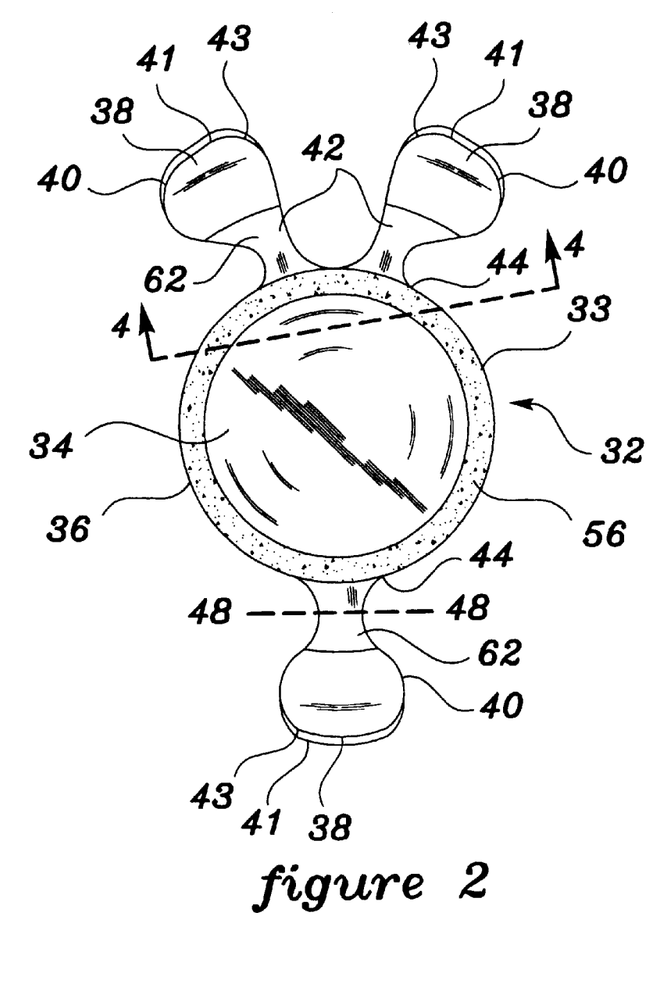
FIG. 2 is a plan view of an accommodating IOL with each optic portion having three flexible attachment components made in accordance with the present invention.
Figure 3:
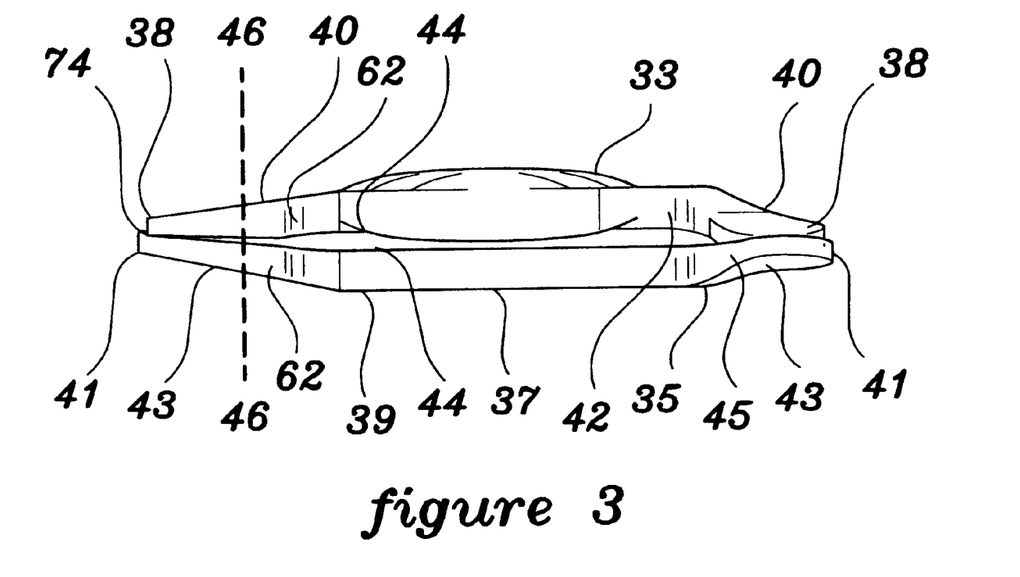
FIG. 3 is a side view of the IOL system of FIG. 2.
Figure 4:
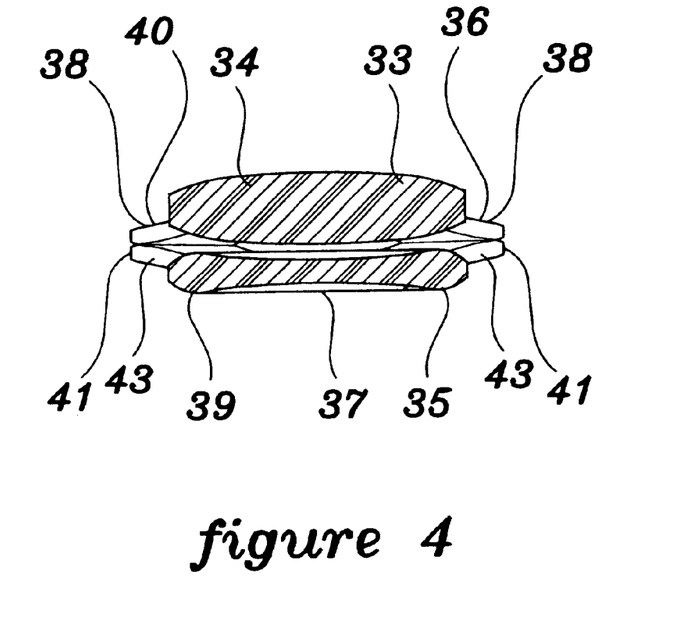
FIG. 4 is a cross sectional view of the IOL system of FIG. 2 taken along line 4—4.
Figure 5:
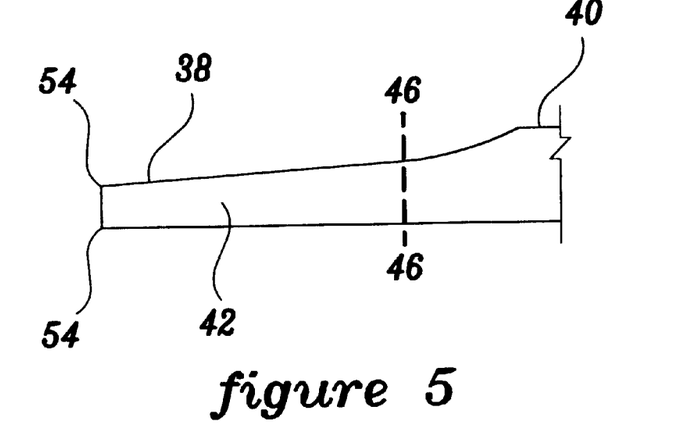
FIG. 5 is a side view of the flexible attachment components of FIG. 3 with sharper edges.
Figures 8, 9:
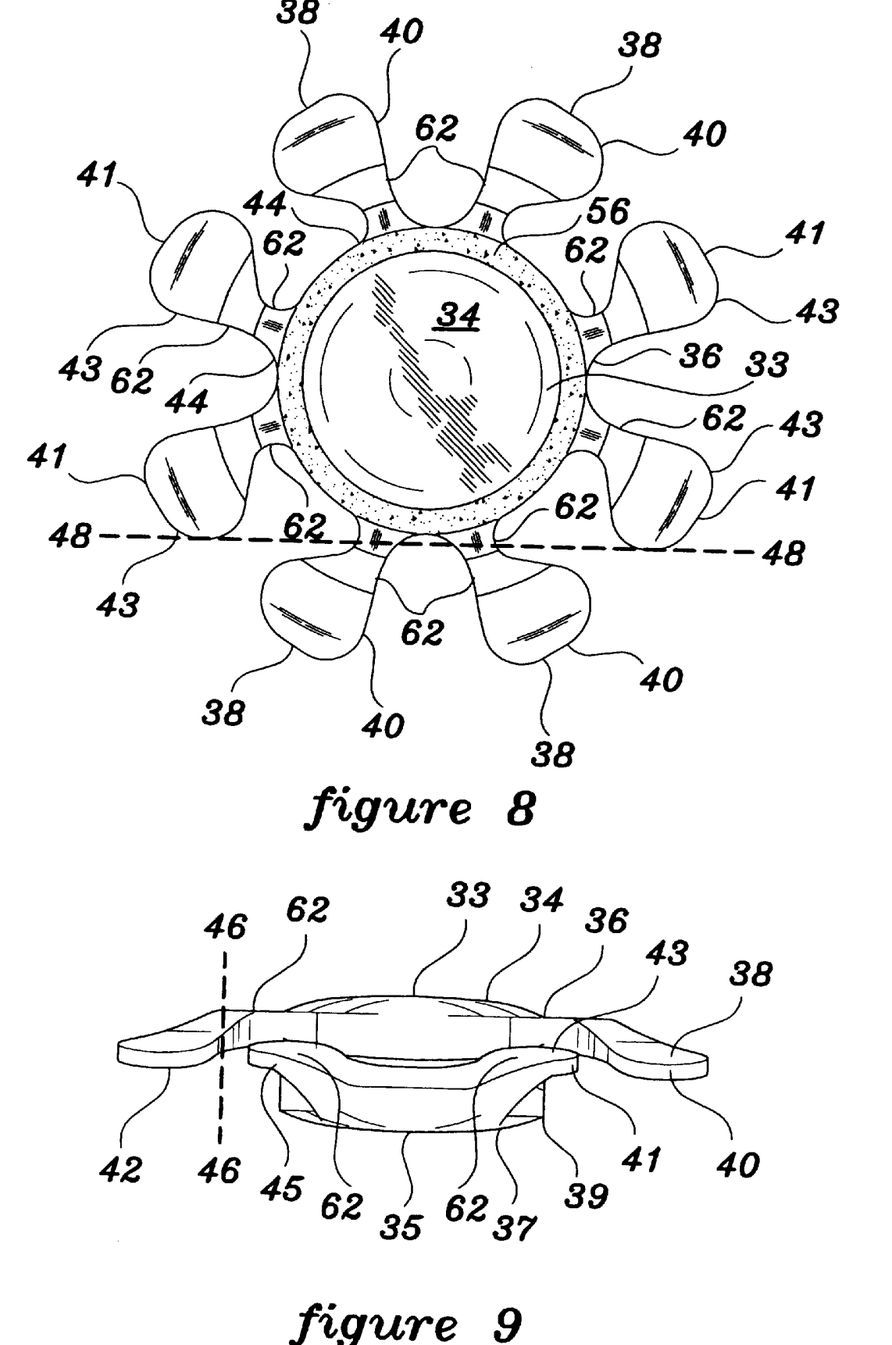
FIG. 8 is a plan view of an accommodating IOL with each optic portion having four flexible attachment components made in accordance with the present invention.
FIG. 9 is a side view of the IOL of FIG. 8.
Figure 10:
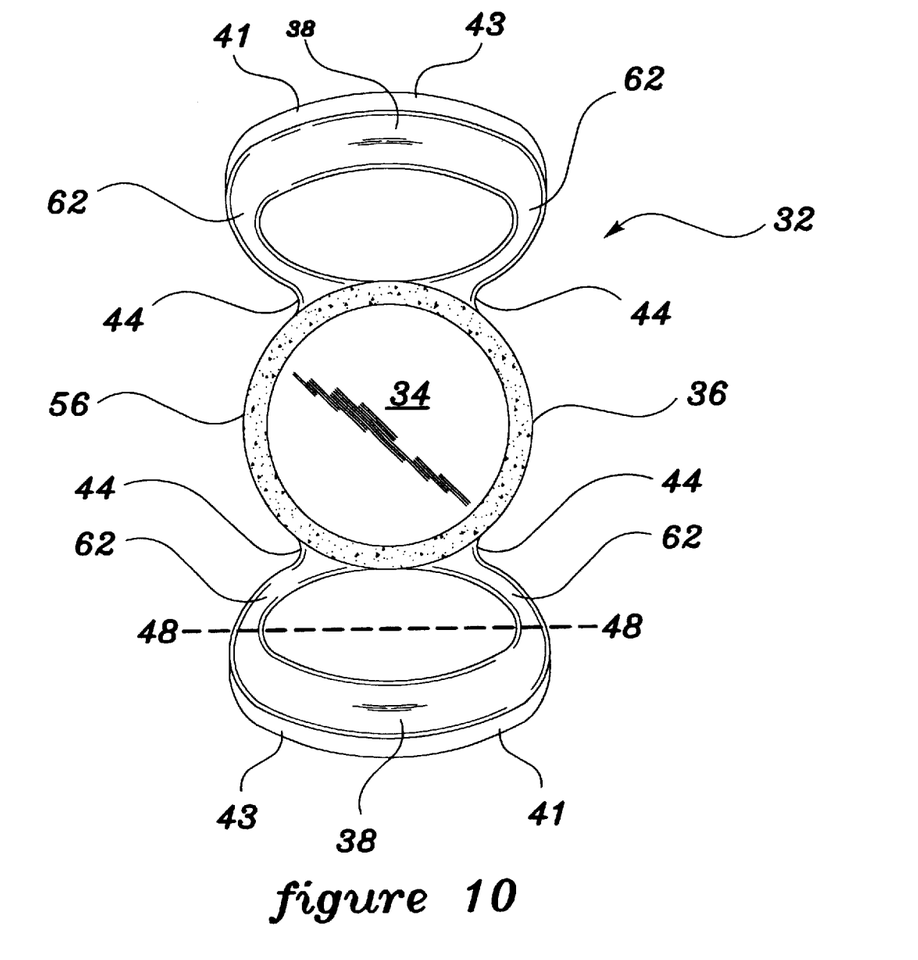
FIG. 10 is a plan view of an accommodating IOL with each optic portion having two flexible attachment components made in accordance with the present invention.
Figure 11:
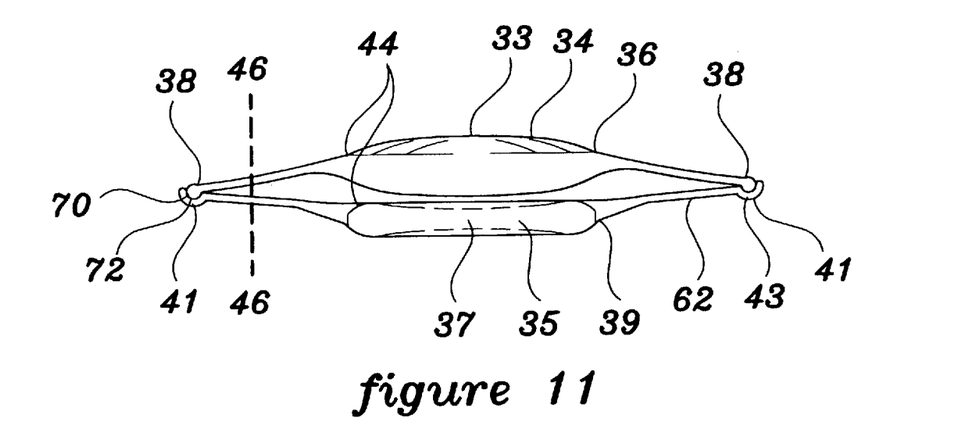
FIG. 11 is a side view of the IOL of FIG. 10.

Accommodating IOL 32 with flexible attachment components 40 of the present invention, as illustrated in FIGS. 2 through 11 but best illustrated in FIGS. 2, 8 and 10, is identified generally by reference numeral 32. Accommodating IOL 32 may be of any suitable design, but for purposes of explanation not limitation, may comprise a positive IOL portion 33 having a higher diopter optic 34 with an outer peripheral edge 36 and a negative IOL portion 35 having a lower diopter optic 37 with an outer peripheral edge 39. Accommodative IOL 32 is designed for implantation preferably in lens capsule 24 of a patient's eye 10. Alternatively, positive IOL portion 33 may be placed in lens capsule 24 and negative IOL portion 35 may be manufactured as a standard anterior chamber intraocular lens to minimize tissue damage, such as that disclosed in U.S. Pat. No. 5,300,117, incorporated herein in its entirety by reference, and positioned within anterior chamber 20. When IOL 32 is positioned within lens capsule 24 of eye 10, positive IOL portion 33 is preferably positioned anterior to negative IOL portion 35 and anteriorly vaulted, i.e., vaulted toward iris 14, and negative IOL portion 35 is positioned posterior to positive IOL portion 33 and posteriorly vaulted, i.e., vaulted toward retina 18. A vault of approximately 1.0 to 2.0 mm measuring from the plane of outer peripheral edges 36 and 39 of optics 34 and 37 respectively to the plane of haptic contact plates 38 and 41 respectively, described in detail below, is generally suitable. Preferably integrally formed on peripheral edges 36 and 39 of optics 34 and 37 are two or more but preferably two, three or four looped or non-looped polyurethane elastomer flexible attachment components 40 and 43 respectively, each having an edge portion 42 and 45 respectively. Polyurethane elastomer flexible attachment components 40 and 43 are preferably integrally formed with and permanently connected to outer peripheral edges 36 and 39 of optics 34 and 37 by attachment portions 44. Alternatively however, flexible attachment components 40 and 43 may be attached to optics 34 and 37 by staking, chemical polymerization or other methods known to those skilled in the art. Each flexible attachment component 40 and 43 also includes a broadened contact plate 38 and 41 respectively designed to preferably engage inner surfaces 50 in lens capsule 24 of eye 10. Broadened contact plates 38 and 41 may be designed for direct contact as illustrated in FIGS. 3 and 11. Such designs may include, but are not limited to, contact plate 41 having a trough 70 and contact plate 38 having a ridge 72 to achieve preferably nonpermanent, but alternatively permanent, interlocking of positive IOL portion 33 and negative IOL portion 35 (FIG. 11) or an extended tab 74 on edge 45 of contact plate 41 to achieve preferably nonpermanent, but alternatively permanent, interlocking with edge 42 of contact plate 38 of positive IOL portion 33 (FIG. 3). As another alternative, best illustrated in FIG. 8, contact plates 38 and 41 of positive IOL portion 33 and negative IOL portion 35 may be positioned so as to avoid direct contact upon placement within lens capsule 24.

In accordance with the present invention, flexible attachment components 40 and 43 are designed so that when IOL 32 is implanted in the lens capsule 24 of a patient's eye 10 and held in place through compressive forces exerted by inner surfaces 50 on contact plates 38 and 41 of flexible attachment components 40 and 43 respectively, flexible attachment components 40 and 43 flex so that contact plates 38 and 41 do not slide along surfaces 50 in eye 10. Accordingly, flexible attachment components 40 and 43 are designed to flex in a plane generally perpendicular to that of optics 34 and 37 of IOL 32 and generally parallel to that of optical axis OA—OA of eye 10. Flexible attachment components 40 and 43 flex to achieve displacement of positive IOL portion 33 with respect to negative IOL portion 35. When IOL 32 is implanted within lens capsule 24, negative IOL portion 35 may be fixed whereby only positive IOL portion 33 is axially displaced to achieve multi-distance visual imaging. However, it is preferable to maximize accommodative effects through opposed axial displacement of both positive and negative IOL portions 33 and 35, respectively. Polyurethane elastomer flexible attachment components 40 and 43 of the present invention enable IOL 32 to achieve maximum, durable, accommodative effect to allow an eye to achieve multi-distance visual imaging without the aid of eyeglasses. The durability of polyurethane elastomer flexible attachment components 40 and 43 enables axial displacement of optics 34 and 37 in opposite directions along optical axis OA—OA of eye 10 millions of times within a patient's lifetime. Compressive forces of differing magnitudes within the range of approximately 0.1 to 5 mN exerted against contact plates 38 and 41 of flexible attachment components 40 and 43 to effect approximately an overall 1.0 mm in diameter compression of IOL 32, such as that caused by natural brain-induced forces within eye 10, results in approximately 1.0 mm to 3.0 mm combined opposed axial displacement of optics 34 and 37 along optical axis OA—OA in an eye 10. By combining a higher diopter positive IOL portion with that of a lower diopter negative IOL portion, an additive effect is achieved whereby even slight movement or axial displacement of the higher diopter positive IOL portion with regard to the lower diopter negative IOL portion results in a disproportionately large increase in accommodative effect and improved multi-distance visual imaging without the aid of eyeglasses. For example, if one were to use a +50 diopter positive IOL portion in conjunction with a −30 diopter negative IOL portion for a combined +20 diopter effect, one achieves at least double the accommodative effect achieved using a single +20 diopter positive IOL. By adding axial displacement of the higher diopter positive IOL portion with respect to the lower diopter negative IOL portion, the accommodative effects of IOL 32 are even greater. The polyurethane elastomer flexible attachment components 40 and 43 of the present invention with their significantly superior durability and flexibility enable maximized accommodative effects through the axial displacement of optic 34 with respect to optic 37 to allow an eye to achieve reliable multi-distance visual imaging when compressive forces are applied to eye 10 without the use of eyeglasses.

Figure 6:
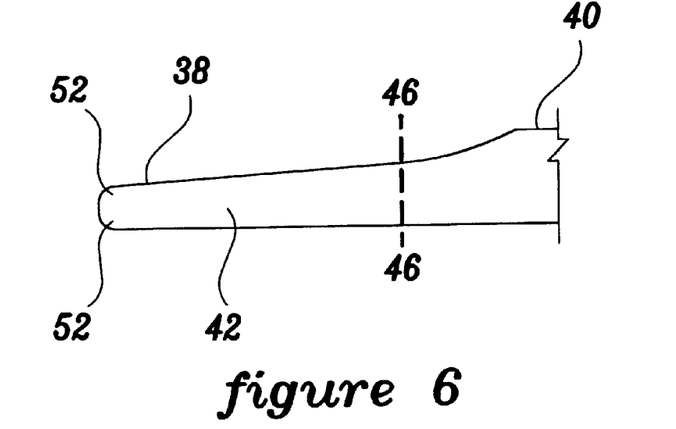
FIG. 6 is a side view of the flexible attachment components of FIG. 3 with rounded edges.

The flexibility characteristics of flexible attachment component 40 and 43 of IOL system 32 as described above are achieved through the material of manufacture and the unique design thereof. As best illustrated in FIG. 2, IOL 32 has flexible attachment components 40 and 43 designed with flexible central portions 62 adjacent to attachment portions 44 permanently connected to outer peripheral edges 36 and 39 of optics 34 and 37 respectively. Flexible central portions 62 are essential in imparting the necessary flexibility to the IOLs. Flexible central portions 62 have a dimension in plane 46—46 generally parallel to optical axis OA—OA, as depicted in FIGS. 3, 9 and 11, less than or equal to but most preferably less than the same in plane 48—48 generally perpendicular to optical axis OA—OA as depicted in FIGS. 2, 8 and 10. Contact plates 38 and 41 are relatively flat with either rounded edges 52 as depicted in FIG. 6 to provide a smoother fit with inner surfaces 50, or more defined, sharper edges 54 as depicted in FIG. 7 to provide a barrier to prevent cellular migration and growth upon implantation in lens capsule 24.

IOL 32 may be manufactured to have optics 34 and 37 approximately 4.5 to 9.0 mm, but preferably approximately 5.0 to 6.0 mm and most preferably approximately 5.5 to 6.0 mm in diameter and approximately 0.15 mm to 1.0 mm, but preferably approximately 0.6 to 0.8 mm and most preferably approximately 0.7 mm in thickness at peripheral edge 36. Flexible attachment components 40 and 43 extend from the optic portions 34 and 37 respectively of IOL system 32 in a generally rounded or oval configuration and increase or decrease in overall length depending on the desired size of IOL 32 and the diameter of optics 34 and 37. As the diameter of optics 34 and/or 37 increase, the overall length of flexible attachment components 40 and/or 43 may decrease. Likewise, as the diameter of optics 34 and/or 37 decrease, the overall length of flexible attachment components 40 and/or 43 may increase. However, as customary, the overall length of the flexible attachment components 40 and 43 are varied to achieve desired IOL 32 sizes rather than varying the sizes of optics 34 and/or 37. In general, looped flexible attachment components 40 and 43 as illustrated in FIGS. 2, 8 and 10 are formed to be approximately 2.6 to 6.0 mm, but preferably approximately 3.4 to 5.0 mm and most preferably approximately 4.2 mm in length measuring from a point of equal distance between common attachment portions 44 on peripheral edges 36 and 39, to the center of contact plates 38 and 41 respectively. Looped flexible attachment components 40 and 43 preferably have a generally rounded or oval configuration as illustrated in FIGS. 10 and 11 to allow axial deflection under compressive forces. Non-looped flexible attachment components 40 and 43 as illustrated in FIGS. 8 and 9 are formed to be approximately 2.6 to 6.0 mm, but preferably approximately 3.4 to 5.0 mm and most preferably approximately 4.2 mm in length measuring from the middle of attachment portion 44 on peripheral edges 36 and 39, to the center of contact plates 38 and 41 respectively. Non-looped flexible attachment components 40 and 43 preferably have a generally rounded or oval configuration as illustrated in FIGS. 8 and 9 to provide a suitable stable fit within lens capsule 24 while allowing axial deflection under compressive forces. For purposes of the present invention, the generally rounded or oval shape of looped and non-looped flexible attachment components 40 and 43, i.e., the beam curve shape, relative to the width to thickness ratio, i.e., the aspect ratio, of flexible attachment components 40 and 43 as described herein is critical to achieve suitable function. Flexible central portion 62 of flexible attachment components 40 and 43 is approximately 0.5 to 2.5 mm, but preferably approximately 1.0 to 2.0 mm and most preferably approximately 1.6 mm in length; approximately 0.2 to 1.0 mm, but preferably approximately 0.3 to 0.7 mm and most preferably approximately 0.46 mm in width in plane 48—48 and approximately 0.2 to 0.7 mm, but preferably approximately 0.3 to 0.6 and most preferably approximately 0.43 mm in thickness in plane 46—46. Contact plates 38 and 41 are approximately 0.8 to 2.5 mm, but preferably approximately 1.0 to 2.2 mm and most preferably approximately 1.8 mm in length, approximately 0.05 to 0.5 mm, but preferably approximately 0.1 to 0.4 mm and most preferably approximately 0.3 mm in thickness and approximately 0.6 to 1.5 mm, but preferably approximately 0.8 to 1.2 mm and most preferably approximately 1.0 mm in width.

As provided through the dimensions of IOL 32 above, looped and non-looped flexible attachment components 40 and 43 are relatively thick in plane 48—48 at contact plates 38 and 41 through to attachment portions 44 and optic portions 34 and 37, with flexible central portions 62 preferably exhibiting a thinner dimension in plane 46—46 than that of the width in plane 48—48. Looped flexible attachment components 40 and 43 of the subject IOL system 32 tend to resist deflection into closer proximity with outer peripheral edges 36 and 39 respectively when a compression force is exerted against contact plates 38 and 41 to maximize axial displacement along optical axis OA—OA. When accommodating IOL 32 is used as a refractive lens, stable, reliable multi-distance visual imaging is provided.

Figure 7:
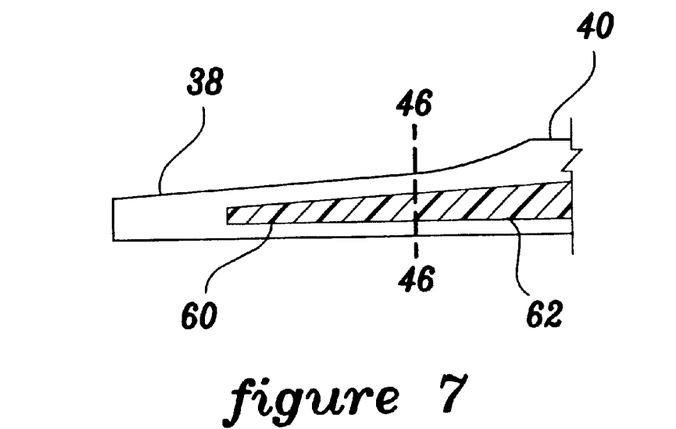
FIG. 7 is a cross sectional view of the flexible attachment components of FIG. 5 with a stiffening element.

The desired flexibility characteristic of flexible attachment components 40 and 43 of IOL 32 may likewise be achieved or enhanced by incorporating a stiffening element 60, in the shape of a wide, very thin ribbon, in one or more flexible attachment components 40 and 43, as illustrated in FIG. 7. Stiffening element 60 may be positioned in flexible attachment components 40 and 43 so that wide or broad flat face 62 is oriented in a plane parallel to that of plane 48—48 so as to be thin axially in a plane parallel to that of plane 46—46. Stiffening element 60 functions in a manner similar to that of an I-beam in construction to maximize axial displacement along optical axis OA—OA when compressive force is applied to contact plates 38 and 41.

Optional stiffening element 60 may be formed of a less flexible polyurethane material than that of IOL system 32. Stiffening element 60 may be fabricated using one or more layers of a mesh, screen, webbing and/or sheet polyurethane material to impart the desired flexibility characteristics described herein. Stiffening element 60 may be used in conjunction with flexible attachment components 40 and 43 described above in cases where a thinner haptic design is desired while still achieving the desired stability and flexibility characteristics. Suitable materials for the production of optics 34 and 37 include but are not limited to foldable or compressible materials, such as silicone polymers, hydrocarbon and fluorocarbon polymers, hydrogels, soft acrylic polymers, polyesters, polyamides, polyurethane, silicone polymers with hydrophilic monomer units, fluorine-containing polysiloxane elastomers and combinations thereof. The preferred material for the production of IOL 32 of the present invention is a hydrophilic or hydrophobic acrylic or silicone with a high refractive index, such as for example approximately 1.474 or greater. A high refractive index is a desirable feature in the production of IOLs to impart high optical power with a minimum of optic thickness. By using a material with a high refractive index, visual acuity deficiencies may be corrected using a thinner IOL. Acrylic and silicone materials are desirable in the production of IOL 32 due to their mechanical strength, which is suitable to withstand considerable physical manipulation.

The polyurethane elastomer material useful for the manufacture of the subject flexible attachment components 40 and 43 is preferably a polyether urethane material and more preferably a polyether urethane urea material such as but not limited to a 2000 molecular weight polytetramethylene glycol, methylene diphenylene diisocyanate and methylene diamine material.

The subject flexible attachment components 40 and 43 may be manufactured by preparing a solution made of polyetherurethane urea in dimethylacetamide. Very thin sheets or curved sections of the polyetherurethane urea material may be made by dip-casting. Dip-casting is achieved by dipping a mandrel into the polyetherurethane urea/dimethylacetamide solution. The thickness of flexible attachment components 40 and 43 is controlled by the number of dips of the mandrel into the solution. Such dip-casting may be suitable for forming curved flexible attachment components 40 and 43 depending on the design desired. Individual flexible attachment components 40 and 43 are cut off the mandrel for attachment to optic portions 34 and 37. A flat sheet of polyetherurethane urea material may be made by pouring the polyetherurethane urea/dimethylacetamide solution onto a flat plate or by using a film casting knife on a flat plate. Individual flexible attachment components 40 and 43 may then be cut or stamped from the sheet.

Once formed, the subject flexible attachment components 40 and 43 may be permanently attached to optic portions 34 and 37 by numerous methods including but not limited to fastening within a pre-formed optic slot 100 using glue, staking, plasma treatment, friction, or like means or combinations thereof.

Although the teachings of the present invention are preferably applied to soft or foldable IOL optics formed of a foldable or compressible material, the same may also be applied to harder, less flexible lens optics formed of a relatively rigid material such as polymethylmethacrylate (PMMA).

Optic 34 of IOL 32 can be a positive powered lens of approximately +20 diopter or greater but preferably approximately +20 to +60 diopter and negative optic 37 of IOL 32 can be a negative powered lens of approximately −10 diopter or less but preferably −10 to −50 diopter. Optics 34 and 37 may be a combination of biconvex, plano-convex, plano-concave, biconcave, concave-convex (meniscus) or a diffractive-type lens element of any shape, depending upon the power required to achieve the appropriate accommodative effects for multi-distance visual imaging and to achieve appropriate central and peripheral thickness for efficient handling and fit within the eye 10. From the perspective of fit within eye 10 and performance, preferably positive IOL portion 33 is convex-plano and negative IOL portion 35 is plano-convex so the plano surface of positive IOL portion 33 is in close proximity to the piano surface of negative IOL portion 35, but most preferably, positive IOL portion 33 is convex-plano and negative IOL portion 35 is concave-plano so the plano surface of positive IOL portion 33 is in close proximity to the concave surface of negative IOL portion 35.

Optics 34 and 37 of the subject IOL 32 may optionally be formed with a glare reduction zone 56 of approximately 0.25 to 2.00 mm but more preferably approximately 0.3 to 0.6 mm and most preferably 0.5 mm in width adjacent outer peripheral edge 36 and 39 for reducing glare when outer peripheral edge 36 and 39 of IOL 32 is struck by light entering eye 10 during high light or at other times when pupil 58 is dilated. Glare reduction zone 56 is typically fabricated of the same material as optics 34 and 37, but may be opaque, colored or patterned in a conventional manner to block or diffuse light in plane with optical axis OA—OA.

IOL 32 may or may not be of a unitary design. Optics 34 and 37 may be molded or most preferably manufactured by first producing disks from a material of choice as described in U.S. Pat. Nos. 5,217,491 and 5,326,506, each incorporated herein in its entirety by reference. If manufactured from disks, positive and negative optics 34 and 37 respectively, are machined from material disks in a conventional manner. Once machined or molded, positive and negative optics 34 and 37 are equipped with flexible attachment components 40 and 43, polished, cleaned, sterilized and packaged by a conventional method known to those skilled in the art.

IOL 32 is used in eye 10 by creating an incision in cornea 12 and capsule 24, removing natural lens 16, inserting negative IOL portion 35 and positive IOL portion 33 as a unitary device or individually into capsule 24 and closing the incision. Preferably, IOL portions 35 and 33 are inserted into capsule 24 individually to allow for easier lens folding and smaller incision size. Alternatively, IOL 32 may be used in eye 10 by creating an incision in cornea 12 and capsule 24, removing natural lens 16, inserting positive IOL portion 33 into capsule 24, inserting negative IOL portion 35 into anterior chamber 20 and closing the incision.

IOL 32 equipped with the polyurethane elastomer flexible attachment means of the present invention provides an accommodating IOL suitable for use in an aphakic eye 10. Flexible attachment means 40 and 43 are durable and have flexibility characteristics that facilitate opposed axial displacement of optics 34 and 37 along optical axis OA—OA of eye 10 thereby enabling an eye to achieve multi-distance visual imaging without the aid of eyeglasses.

While there is shown and described herein certain specific embodiments of the present invention, it will be manifest to those skilled in the art that various modifications may be made without departing from the spirit and scope of the underlying inventive concept and that the same is not limited to the particular forms herein shown and described except insofar as indicated by the scope of the appended claims.

I claim:

1. An accommodating intraocular lens to be implanted within an eye generally perpendicular to the eye's optical axis comprising:
   a first outer peripheral edge defining a higher diopter positive optic with two or more polyurethane elastomer flexible attachment components permanently connected to the first outer peripheral edge to form a positive lens, and
   a second outer peripheral edge defining a lower diopter negative optic with two or more polyurethane elastomer flexible attachment components permanently connected to the second outer peripheral edge to form a negative lens, to enable a compressive force sufficient to effect a 1.0 mm in diameter compression of said positive lens to result in approximately 1.0 mm of axial displacement of said positive optic with respect to said negative optic along the eye's optical axis to enable an eye to achieve multi-distance visual imaging.

2. An accommodating intraocular lens to be implanted within an eye generally perpendicular to the eye's optical axis comprising:
   a first outer peripheral edge defining a higher diopter positive optic with two or more polyurethane elastomer flexible attachment components permanently connected to the first outer peripheral edge to form a positive lens, and
   a second outer peripheral edge defining a lower diopter negative optic with two or more polyurethane elastomer flexible attachment components permanently connected to the second outer peripheral edge to form a negative lens, to enable a compressive force sufficient to effect a 1.0 mm in diameter compression of said positive lens to result in approximately 1.5 mm of axial displacement of said positive optic with respect to said negative optic along the eye's optical axis to enable an eye to achieve multi-distance visual imaging.

3. An accommodating intraocular lens to be implanted within an eye generally perpendicular to the eye's optical axis comprising:
   a first outer peripheral edge defining a higher diopter positive optic with two or more polyurethane elastomer flexible attachment components permanently connected to the first outer peripheral edge to form a positive lens, and
   a second outer peripheral edge defining a lower diopter negative optic with two or more polyurethane elastomer flexible attachment components permanently connected to the second outer peripheral edge to form a negative lens, to enable a compressive force sufficient to effect a 1.0 mm in diameter compression of said positive lens to result in approximately 2.0 mm of axial displacement of said positive optic with respect to said negative optic along the eye's optical axis to enable an eye to achieve multi-distance visual imaging.

4. An accommodating intraocular lens to be implanted within an eye generally perpendicular to the eye's optical axis comprising:
   a first outer peripheral edge defining a higher diopter positive optic with two or more polyether urethane elastomer flexible attachment components permanently connected to the first outer peripheral edge to form a positive lens, and
   a second outer peripheral edge defining a lower diopter negative optic with two or more polyether urethane elastomer flexible attachment components permanently connected to the second outer peripheral edge to form a negative lens.

5. The accommodating intraocular lens of claim 1, 2, 3 or 4 wherein said flexible attachment components are manufactured from a polyether urethane urea or a 2000 molecular weight polytetramethylene glycol, methylene diphenylene diisocyanate and methylene diamine material.

6. The accommodating intraocular lens of claim 1, 2, 3 or 4 wherein said negative optic is fixed.

7. The accommodating intraocular lens of claim 1, 2, 3 or 4 wherein said negative optic is axially displaced upon compression.

8. The accommodating intraocular lens of claim 1, 2, 3 or 4 wherein said negative lens and said positive lens are both configured to be implanted within a lens capsule of said eye.

9. The accommodating intraocular lens of claim 1, 2, 3 or 4 wherein said negative lens is configured to be implanted in an anterior chamber of an eye and said positive lens is configured to be implanted within a lens capsule of said eye.

10. The accommodating intraocular lens of claim 1, 2, 3 or 4 wherein said optics are formed of a foldable or compressible material.

11. The accommodating intraocular lens of claim 1, 2, 3 or 4 wherein said positive and negative optics are formed from one or more of the same or differing materials selected from the group consisting of silicone polymers, hydrocarbon polymers, fluorocarbon polymers, hydrogels, soft acrylic polymers, polyester, polyamides, polyurethane, silicone polymers with hydrophilic monomer units and fluorine-containing polysiloxane elastomers.

12. The accommodating intraocular lens of claim 1, 2, 3 or 4 wherein either one or both of said positive and negative optics are formed from a hydrophilic or hydrophobic acrylic material.

13. The accommodating intraocular lens of claim 1, 2, 3 or 4 wherein either one or both of said positive and negative optics are formed from a silicone material.

14. The accommodating intraocular lens of claim 1, 2, 3 or 4 wherein either one or both of said positive and negative optics are formed from a material having a refractive index above approximately 1.474.

15. The accommodating intraocular lens of claim 1, 2, 3 or 4 wherein said flexible attachment components are formed with a dimension in a plane generally perpendicular to the eye's optical axis to be greater than or equal to a dimension in a plane generally parallel to the eye's optical axis.

16. The accommodating intraocular lens of claim 1, 2, 3 or 4 wherein a glare reduction zone is formed adjacent to the outer peripheral edge of either one or both of said optics.

17. The accommodating intraocular lens of claim 1, 2, 3 or 4 wherein one or more of said flexible attachment components includes a stiffening element having less resistance to bending in a plane generally parallel to an eye's optical axis than in a plane generally perpendicular to the eye's optical axis.

18. The accommodating intraocular lens of claim 1, 2, 3 or 4 wherein one or more of said flexible attachment components includes a stiffening element formed from a polyurethane material.

19. A method of manufacturing the accommodating intraocular lens of claim 1, 2, 3 or 4 comprising:

forming two disks from the same or different suitable materials, machining a positive optic from one disk, machining a negative optic from the other disk, and permanently or non-permanently connecting said optics with two or more polyurethane or polyether urethane elastomer flexible attachment components.

20. A method of manufacturing the accommodating intraocular lens of claim 1, 2, 3 or 4 comprising:

molding a positive optic of a suitable material, molding a negative optic of a suitable material, and permanently or non-permanently connecting said optics with two or more polyurethane or polyether urethane elastomer flexible attachment components.

21. A method of using the accommodating intraocular lens of claim 1, 2, 3 or 4 comprising:

creating an incision in a cornea and lens capsule of an eye, removing a natural lens of said eye, and inserting a lower diopter negative intraocular lens and a higher diopter positive intraocular lens into said lens capsule of said eye as either individual lenses or as a unitary device.

22. A method of using the accommodating intraocular lens of claim 1, 2, 3 or 4 comprising:

creating an incision in a cornea and lens capsule of an eye, removing a natural lens of said eye, inserting a higher diopter positive intraocular lens into said lens capsule of said eye, and inserting a lower diopter negative intraocular lens into an anterior chamber of said eye.

23. A method of using the accommodating intraocular lens of claim 1, 2, 3 or 4 comprising:

creating an incision in a cornea and lens capsule of an eye, removing a natural lens of said eye, inserting a lower diopter negative intraocular lens into said lens capsule, and inserting a higher diopter positive intraocular lens into said lens capsule of said eye anterior to said lower diopter negative intraocular lens.

\* \* \* \* \*